United States Patent
Dierker et al.

(10) Patent No.: US 10,449,135 B2
(45) Date of Patent: Oct. 22, 2019

(54) SOLUBLIZING AGENTS FOR UV FILTERS IN COSMETIC FORMULATIONS

(71) Applicant: BASF SE, Ludwigshafen (DE)

(72) Inventors: Markus Dierker, Düsseldorf (DE); Jochen Giesinger, Grenzach-Wyhlen (DE)

(73) Assignee: BASF SE (DE)

( * ) Notice: Subject to any disclaimer, the term of this patent is extended or adjusted under 35 U.S.C. 154(b) by 0 days.

(21) Appl. No.: 15/302,750

(22) PCT Filed: Apr. 1, 2015

(86) PCT No.: PCT/EP2015/057213
§ 371 (c)(1),
(2) Date: Oct. 7, 2016

(87) PCT Pub. No.: WO2015/155095
PCT Pub. Date: Oct. 15, 2015

(65) Prior Publication Data
US 2017/0027831 A1 Feb. 2, 2017

(30) Foreign Application Priority Data

Apr. 9, 2014 (EP) .................................... 14164063

(51) Int. Cl.
| | |
|---|---|
| *A61K 8/49* | (2006.01) |
| *A61K 8/37* | (2006.01) |
| *A61K 8/42* | (2006.01) |
| *A61K 8/41* | (2006.01) |
| *A61Q 17/04* | (2006.01) |

(52) U.S. Cl.
CPC .................. *A61K 8/49* (2013.01); *A61K 8/37* (2013.01); *A61K 8/415* (2013.01); *A61K 8/42* (2013.01); *A61K 8/4913* (2013.01); *A61K 8/4926* (2013.01); *A61K 8/4946* (2013.01); *A61K 8/4966* (2013.01); *A61Q 17/04* (2013.01); *A61K 2800/49* (2013.01)

(58) Field of Classification Search
None
See application file for complete search history.

(56) References Cited

U.S. PATENT DOCUMENTS

| | | | |
|---|---|---|---|
| 4,595,458 A * | 6/1986 | Frentzel | D21H 17/07 162/135 |
| 5,338,539 A | 8/1994 | Raspanti | |
| 5,518,713 A | 5/1996 | Raspanti | |
| 5,601,811 A | 2/1997 | Gallagher et al. | |
| 5,955,060 A | 9/1999 | Hüglin et al. | |
| 6,193,959 B1 | 2/2001 | Bernasconi et al. | |
| 6,255,279 B1 * | 7/2001 | Christophers | A61K 8/04 424/401 |
| 6,365,637 B1 | 4/2002 | Zirnstein et al. | |
| 6,409,998 B1 | 6/2002 | Candau et al. | |
| 6,440,401 B1 | 8/2002 | Heywang et al. | |
| 7,074,922 B2 | 7/2006 | Gumbel et al. | |
| 7,101,563 B1 * | 9/2006 | Vromen | A61K 9/0014 424/401 |
| 7,816,520 B2 | 10/2010 | Picoul et al. | |
| 2004/0247536 A1 | 12/2004 | Chaudhuri | |
| 2005/0075265 A1 * | 4/2005 | De Salvert | A61K 8/03 510/407 |

(Continued)

FOREIGN PATENT DOCUMENTS

| | | |
|---|---|---|
| CH | 401469 A | 10/1965 |
| DE | 1165574 B | 3/1964 |

(Continued)

OTHER PUBLICATIONS

Manabe Agricultural and Biological Chemistry 1987 51(7):1959-1965 (Year: 1987).*
U.S. Appl. No. 15/302,796, filed Oct. 7, 2016, BASF SE.
"New solubilizers for organic UV filters in Personal Care—an IP.com Prior Art Database Technical Disclosure", retrieved from ip.com/pdf/ipcompad/IPCOM000158883D.pdf, dated Oct. 4, 2007.
International Search Report for PCT/EP2015/057213 dated Jun. 9, 2015.

(Continued)

*Primary Examiner* — Robert A Wax
*Assistant Examiner* — Caralynne E Helm
(74) *Attorney, Agent, or Firm* — Drinker Biddle & Reath LLP

(57) ABSTRACT

Disclosed is the use of the compounds (A) corresponding to formula

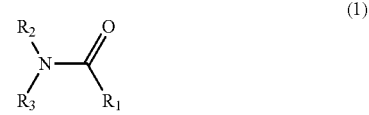

(1)

wherein
$R_1$ represents $C_6$-$C_{24}$ alkyl;
$R_2$ is hydrogen; or $C_1$-$C_4$ alkyl;
$R_3$ is a radical of formula (1a) *—$(CH_2)_{n_1}$—$R_4$
$R_4$ is a heterocyclic or aromatic radical comprising 4 to 6 carbon atoms which can contain from 1 to 3 nitrogen and/or oxygen atoms;
$n_1$ is a number from 0 to 5; or
$R_2$ and $R_3$ together with the linking nitrogen atom form a heterocyclic radical comprising 4 to 6 carbon atoms which can contain one or more oxygen or nitrogen atoms;
as solubilizing agent for organic UV filters (B) selected from
(B1) benzophenone derivatives,
(B2) hydroxyphenyl triazine derivatives; and
(B3) trianilino-s-triazine derivatives.

18 Claims, No Drawings

(56) References Cited

U.S. PATENT DOCUMENTS

| | | | |
|---|---|---|---|
| 2006/0002872 A1* | 1/2006 | Candau | A61K 8/37 424/59 |
| 2006/0193779 A1* | 8/2006 | Loveridge | A61K 6/002 424/9.6 |
| 2007/0219275 A1* | 9/2007 | Baschong | A61K 8/445 514/678 |
| 2010/0209463 A1 | 8/2010 | Pfluecker et al. | |
| 2010/0303744 A1* | 12/2010 | Breyfogle | A61K 8/06 424/59 |
| 2012/0282197 A1* | 11/2012 | Muller | A61K 8/4926 424/59 |
| 2014/0051036 A1* | 2/2014 | Wagner-Doebler | A61K 6/0067 433/202.1 |
| 2015/0050223 A1 | 2/2015 | Perier et al. | |

FOREIGN PATENT DOCUMENTS

| | | | | |
|---|---|---|---|---|
| DE | 2024051 A1 | 12/1971 | | |
| DE | 19851777 A1 | 5/2000 | | |
| DE | 10138496 A1 | 2/2003 | | |
| DE | 10229995 A1 | 1/2004 | | |
| DE | 102007035567 A1 | 1/2009 | | |
| EP | 268222 A2 * | 5/1988 | | |
| EP | 582189 A2 | 2/1994 | | |
| EP | 613893 A1 | 9/1994 | | |
| EP | 0709080 A1 | 5/1996 | | |
| EP | 775698 A1 | 5/1997 | | |
| EP | 0893119 A1 | 1/1999 | | |
| EP | 1093796 A1 | 4/2001 | | |
| EP | 1167358 A1 | 1/2002 | | |
| EP | 1371356 A2 | 12/2003 | | |
| EP | 1371357 A2 | 12/2003 | | |
| EP | 1371358 A2 | 12/2003 | | |
| EP | 1483250 A1 | 12/2004 | | |
| FR | 2252840 A1 | 6/1975 | | |
| FR | 2477873 A1 | 9/1981 | | |
| FR | 2986154 A1 | 8/2013 | | |
| GB | 962919 A | 7/1964 | | |
| GB | 1316733 A * | 5/1973 | | A61K 9/7015 |
| GB | 1333475 A | 10/1973 | | |
| GB | 1494915 A | 12/1977 | | |
| JP | S50-28500 B * | 9/1975 | | |
| KR | 20120077767 A * | 7/2012 | | |
| WO | WO-9700851 A1 | 1/1997 | | |
| WO | WO-9966896 A1 | 12/1999 | | |
| WO | WO-0025731 A1 | 5/2000 | | |
| WO | WO-0185124 A1 | 11/2001 | | |
| WO | WO-0239974 A1 | 5/2002 | | |
| WO | WO-0341675 A2 | 5/2003 | | |
| WO | WO-03074499 A1 | 9/2003 | | |
| WO | WO-2005121128 A1 | 12/2005 | | |
| WO | WO-2009012871 A2 | 1/2009 | | |
| WO | WO-2011038776 A1 | 4/2011 | | |

OTHER PUBLICATIONS

International Search Report for PCT/EP2015/057455 dated Sep. 17, 2015.

E. Chatelain et al., "Skin penetration and sun protection factor of five UV filters: effect of the vehicle", Kin Pharmacol Appl Kin Physiol, 16(1): 28-35, Jan.-Feb. 2003, see Abstact.

* cited by examiner

SOLUBLIZING AGENTS FOR UV FILTERS IN COSMETIC FORMULATIONS

CROSS-REFERENCE TO RELATED APPLICATIONS

This application is a national stage application (under 35 U.S.C. § 371) of PCT/EP2015/057213, filed Apr. 1, 2015, which claims benefit of European Application No. 14164063.1, filed Apr. 9, 2014, both of which are incorporated herein by reference in their entirety.

The present invention relates to the use of specific amide oils as solubilizing agents for dissolving organic UV filters and the use of these materials in cosmetically acceptable products for improved protection against UV radiation as well as cosmetic formulations exhibiting enhanced UV protection performance.

It is well known that ultraviolet radiation (light) is harmful to human skin. Depending on the wavelength the UV radiation causes different types of skin damage. UV-B radiation (about 290 to about 320 nm) is responsible for sunburn and can cause skin cancer. UV-A radiation (about 320 to about 400 nm) while producing tanning of the skin, contributes also to sunburn and the induction of skin cancers. Moreover, the harmful effects of the UV-B radiation may be aggravated by UV-A radiation.

Therefore, an effective sunscreen formulation preferably comprises both at least one UV-A, UV-B filter and a broad band UV filter covering the full range of about 290 nm to about 400 nm to prevent the human skin from damaging by the sunlight.

Very effective organic UV filters covering the full UV-A/UV-B range are the classes of benzophenone derivatives, hydroxyphenyl triazine derivatives; and trianilino-s-triazine derivatives.

Unfortunately, these UV absorber have a poor oil-solubility at a certain concentration and tend to crystallization. As a consequence the UV protection efficacy is significantly decreased.

Moreover the oil soluble UV filter s should be included in cosmetic sun care products without any impact on the sensorial characteristic of the emulsion. For that reason the optimal distribution of the UV absorber within the hydro-lipid film left on the skin after spreading should be guaranteed.

It is therefore an object of the present invention to find UV absorber formulations which have improved performance regarding the UV absorber contained in these formulation.

Surprisingly it was found that certain amide oils guarantee the optimal distribution of the organic UV absorbers within the hydro-lipid film of the UV absorber formulation left on the skin after spreading and promote the highest degree of solubilization of the organic UV absorbers.

Therefore, the present invention relates to the use of the compounds (A) of formula

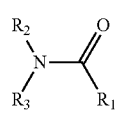

(1)

wherein
$R_1$ represents $C_6$-$C_{24}$alkyl;
$R_2$ is hydrogen; or $C_1$-$C_4$alkyl;
$R_3$ is a radical of formula (1a) *—$(CH_2)_{n1}$—$R_4$
$R_4$ is a heterocyclic or aromatic radical comprising 4 to 6 carbon atoms which optionally contain from 1 to 3 nitrogen and/or oxygen atoms;
$n_1$ is a number from 0 to 5; or
$R_2$ and $R_3$ together with the linking nitrogen atom form a heterocyclic radical comprising 4 to 6 carbon atoms which optionally contain one or more oxygen or nitrogen atoms;
as solubilizing agent for organic UV filters (B) selected from
(B1) benzophenone derivatives,
(B2) hydroxyphenyl triazine derivatives; and
(B3) trianilino-s-triazine derivatives.

$C_1$-$C_4$alkyl and $C_6$-$C_{24}$alkyl are straight-chain or branched alkyl radicals such as methyl, ethyl, n-propyl, isopropyl, n-butyl, sec-butyl, tert. butyl, hexyl, heptyl, octyl, isooctyl, nonyl, decyl, undecyl, dodecyl, tetradecyl, pentadecyl, hexadecyl, heptadecyl or octadecyl.

Preferably in formula (1)
$R_4$ is a radical of formula

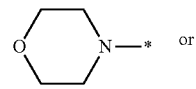

(1b)

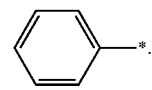

(1c)

More preferred compounds of formula (1) are those, wherein
$R_3$ is propylmorpholino; or benzyl.

More preferred are also compound of formula (1), wherein
$R_2$ is hydrogen

Further preferred are those compounds of formula (1), wherein
$R_2$ and $R_3$ together with the linking nitrogen atom form a —$(CH_2)_{n2}$— ring which may be substituted with one or more $C_1$-$C_4$alkyl groups and/or interrupted with one or more —O— or —NH; wherein
$n_2$ is a number from 3 to 6.

More preferred are compounds of formula (1) wherein $R_2$ and $R_3$ form a morpholine ring, which may be substituted by one or more $C_1$-$C_4$alkyl.

Further preferred are compounds of formula (1) wherein $R_2$ and $R_3$ together with the linking nitrogen form a 4 to 6-membered heteroaromatic radical which may be substituted by one or more $C_1$-$C_4$alkyl and which may contain one or more nitrogen atoms.

Further preferred are compounds of formula (1) wherein $R_2$ and $R_3$ together with the linking nitrogen form an imidazole ring which may be substituted by one or more than one $C_1$-$C_4$alkyl.

Most preferred are compounds of formula (1) wherein $R_2$ and $R_3$ together with the linking nitrogen form a radical of formula

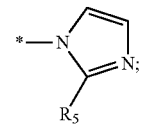

(1d)

wherein

R$_5$ is hydrogen; of C$_1$-C$_5$alkyl.

Preferably in the compounds of formula (1)

R$_1$ is C$_6$-C$_{18}$alkyl, more preferably n-nonyl or n-undecyl; and most preferably n-heptyl, Most preferably the compound of formula (1) corresponds to the compound of formula

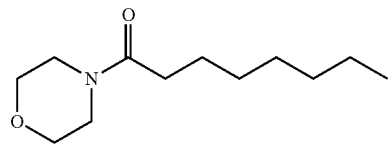

(AM-01)

Preferred are also compounds of formula

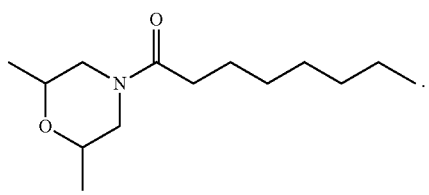

(AM-02)

In Table 1 examples of the compounds (A) according to the present invention are listed.

TABLE 1

| Examples of compounds (A) | | | |
|---|---|---|---|
| Compound | R$_1$ | R$_2$ | R$_3$ |
| (AM-01) | n-heptyl | | R$_2$ + R$_3$ + N |
| (AM-02) | n-nonyl | | (morpholine) |
| (AM-03) | n-undecyl | | |
| (AM-04) | n-heptyl | | R$_2$ + R$_3$ + N |
| (AM-05) | n-nonyl | | (2,6-dimethylmorpholine) |
| (AM-06) | n-undecyl | | |
| (AM-07) | n-heptyl | | R$_2$ + R$_3$ + N |
| (AM-08) | n-nonyl | | (piperidine) |
| (AM-09) | n-undecyl | | |
| (AM-10) | n-heptyl | | R$_2$ + R$_3$ + N |
| (AM-11) | n-nonyl | | (pyrrolidine) |
| (AM-12) | n-undecyl | | |

TABLE 1-continued

| Examples of compounds (A) | | | |
|---|---|---|---|
| Compound | R$_1$ | R$_2$ | R$_3$ |
| (AM-13) | n-heptyl | | R$_2$ + R$_3$ + N |
| (AM-14) | n-nonyl | | (imidazole with R$_5$) |
| (AM-15) | n-undecyl | | |
| (AM-16) | n-heptyl | H | (morpholinoethyl) |
| (AM-17) | n-nonyl | H | |
| (AM-18) | n-undecyl | H | |
| (AM-19) | n-heptyl | H | (benzyl) |
| (AM-20) | n-nonyl | H | |
| (AM-21) | n-undecyl | H | |

Preferably the organic UV filters (B) are used in admixtures of at least two different UV filters selected from (B1), (B2) and (B3).

Preferred benzophenone derivatives (B1) correspond to the formula (BPH-01)

wherein

R$_1$ and R$_2$ independently from each other are hydrogen; C$_1$-C$_{20}$alkyl; C$_3$-C$_{10}$cycloalkyl; or C$_3$-C$_{10}$cycloalkenyl, wherein the radicals R$_1$ and R$_2$ together with the nitrogen atom, to which they are bonded may form a 5- or 6-membered ring; and R$_3$ is C$_1$-C$_{20}$alkyl.

Most preferred benzophenone derivatives (B1) according to the present invention correspond to the formula

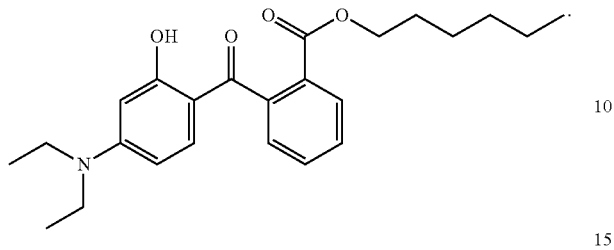

(BPH-02)

Preferred hydroxyphenyl triazine derivatives (B2) according to the present invention correspond to formula

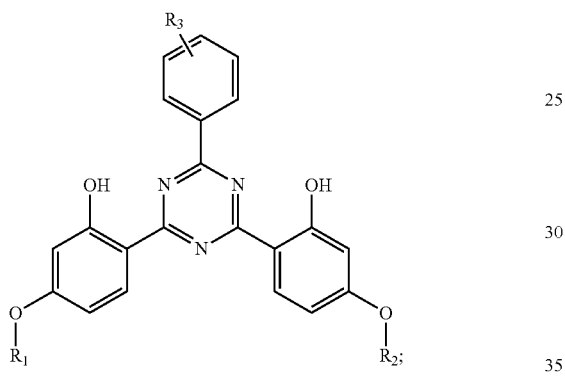

(HTP-01)

wherein
$R_1$ and $R_2$ independently from each other are $C_1$-$C_{18}$alkyl; and
$R_3$ is $C_1$-$C_{10}$alkoxy.

Most preferred hydroxyphenyl triazine derivatives (B2) according to the present invention correspond to formula

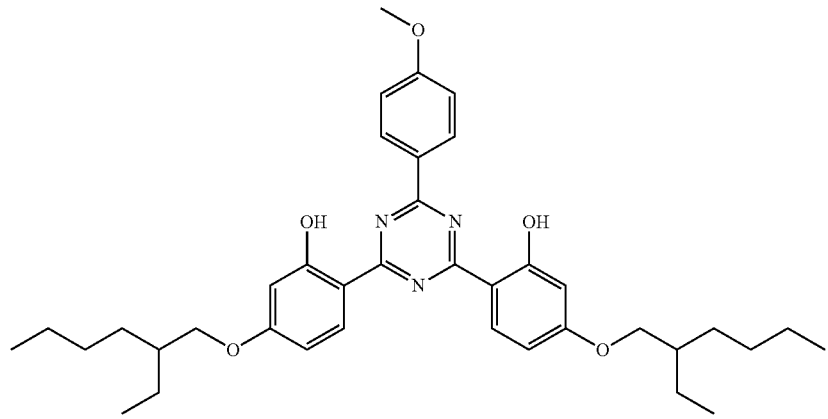

(HTP-02)

Further preferred hydroxyphenyl triazine derivatives (B2) according to the present invention correspond to formula (HTP-03)

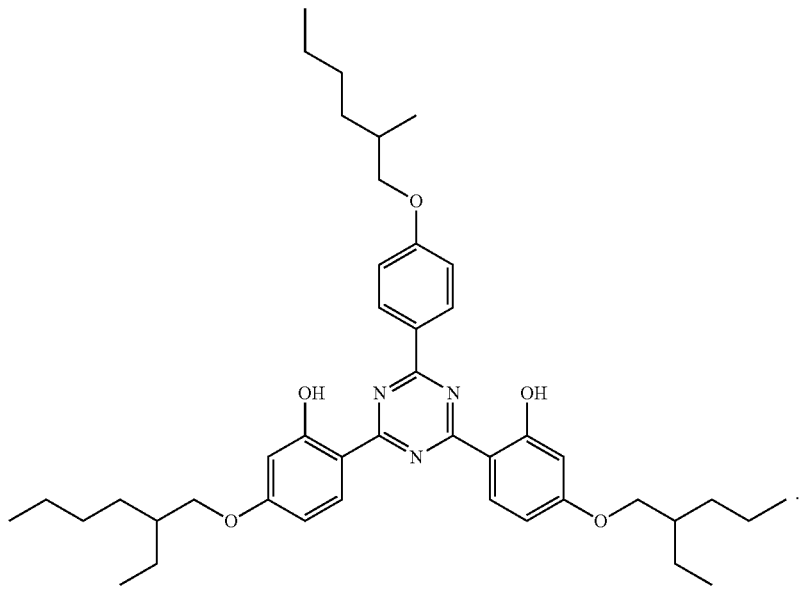

The hydroxyphenyl triazine derivatives (B2) as used in the present invention can be prepared by manners known per se, as described for example in EP 775698 B1.

Preferred trianilino-s-triazine derivatives (B3) correspond to the formula (TAT-01)

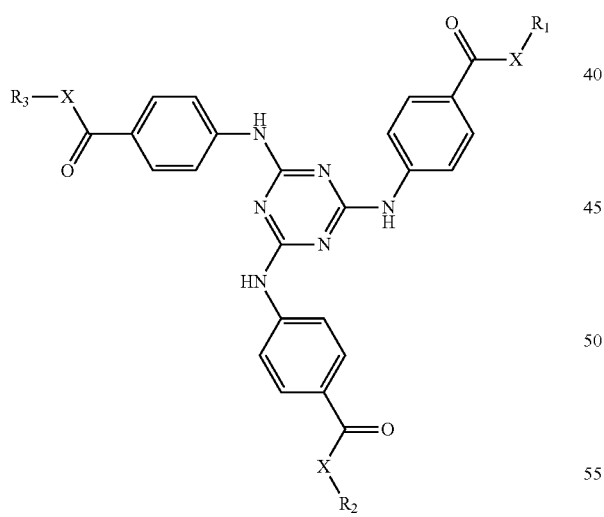

wherein $R_1$, $R_2$ and $R_3$ independently from each other are optionally substituted $C_1$-$C_{20}$alkyl, $C_6$-$C_{10}$aryl or $C_6$-$C_{10}$heteroaryl;

X is O; or $NR_4$; and $R_4$ is hydrogen; or optionally substituted $C_1$-$C_{20}$alkyl, aryl or heteroaryl.

Most preferred trianilino-s-triazine derivatives (B3) correspond to the formula (TAT-02)

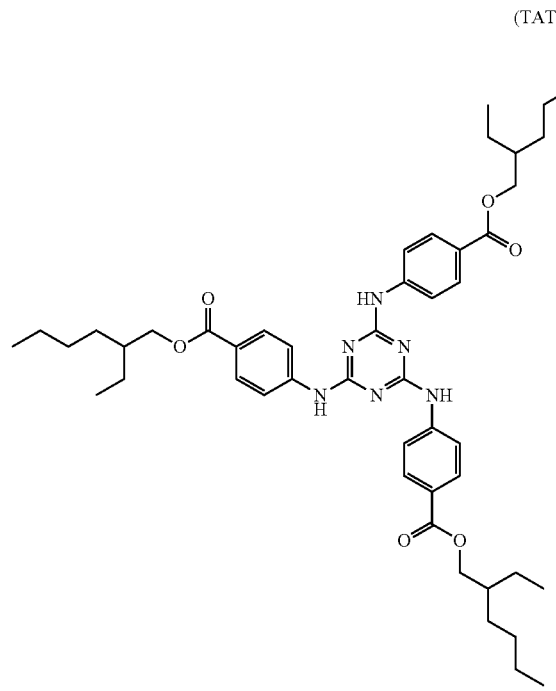

The trianilino-s-triazine derivatives (B3) can be prepared by manners known per se, as described for example in EP1483250.

Preferably the organic UV filters (B) according to the present invention are used as mixtures.

Preferably mixtures of UV filters (BPH-02), (HTP-02) and (TAT-02) are used.

Further preferred mixtures of organic UV filters according to the present invention are:
UV filters (BPH-02) and (HTP-02);
UV filters (BPH-02) and (TAT-02); and
UV filters (HTP-02) and (TAT-02).

Most preferably the compound of formula (AM-01) is used as solubilizing agent (A) for the UV filters (B) selected from (BPH-02), (HTP-02) and (TAT-02).

Furthermore, the present invention relates to a cosmetic composition, which preferably comprises
(A) a solubilizing agent according to formula

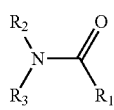 (1)

wherein
$R_1$ represents $C_6$-$C_{24}$alkyl;
$R_2$ is hydrogen; or $C_1$-$C_4$alkyl;
$R_3$ is a radical of formula (1a) *—$(CH_2)_{n1}$—$R_4$
$R_4$ is a heterocyclic or aromatic radical comprising 4 to 6 carbon atoms which can contain from 1 to 3 nitrogen and/or oxygen atoms;
$n_1$ is a number from 0 to 3; or
$R_2$ and $R_3$ together with the linking nitrogen atom form a heterocyclic radical comprising 4 to 6 carbon atoms which can contain one or more oxygen or nitrogen atoms; and (B) at least one organic UV filter selected from
(B1) benzophenone derivatives;
(B2) hydroxyphenyl triazine derivatives; and
(B3) trianilino-s-triazine derivatives.

The cosmetic composition of the present invention preferably comprises
0.1 to 25% b.w. of a solubilizing agent (A);
0.1 to 20% b.w. of a organic UV filter (B); and
10 to 90% b.w. of a cosmetically acceptable carrier (C),
based on the total weight of the cosmetic end-product composition.

Preferably the cosmetic composition comprises a solubilizing agent (A) of formula (AM-01).

Preferably the cosmetic composition comprises
(A) a solubilizing agent of formula (AM-01); and
(B) organic UV filters selected from (HTP-02), (BPH-02) and (TAT-02).

Preferred are also cosmetic compositions, comprising
(A) a solubilizing agent of formula (AM-01) and (B) mixtures of UV filters (HTP-02), (BPH-02) and (TAT-02).
(A) a solubilizing agent of formula (AM-01) and (B) mixtures of UV filters (BPH-02) and (HTP-02).
(A) a solubilizing agent of formula (AM-01) and (B) mixtures of UV filters (HTP-02) and (TAT-02).
(A) a solubilizing agent of formula (AM-01) and (B) mixtures of UV filters (BPH-02) and (TAT-02).

The cosmetic composition according to the present invention may comprise one or more than one additional UV absorbers (component (D)) as described in the Tables 1 and 2.

TABLE 1

Suitable UV filter substances which can be additionally used with the organic UV absorbers (B) according to the present invention p-aminobenzoic acid derivatives, for example 4-dimethylaminobenzoic acid 2-ethylhexyl ester;
salicylic acid derivatives, for example salicylic acid 2-ethylhexyl ester;
benzophenone derivatives, for example 2-hydroxy-4-methoxybenzophenone and its 5-sulfonic acid derivative;
diphenylacrylates, for example 2-ethylhexyl 2-cyano-3,3-diphenylacrylate, and 3-(benzo-furanyl) 2-cyanoacrylate;
3-imidazol-4-ylacrylic acid and esters;
benzofuran derivatives, especially 2-(p-aminophenyl)benzofuran derivatives, described in EP-A-582 189, U.S. Pat. No. 5,338,539, U.S. Pat. No. 5,518,713 and EP-A-613 893;
polymeric UV absorbers, for example the benzylidene malonate derivatives described in EP-A-709 080;
cinnamic acid derivatives, for example the 4-methoxycinnamic acid 2-ethylhexyl ester and isoamyl ester or cinnamic acid derivatives described in U.S. Pat. No. 5,601,811 and WO 97/00851;
camphor derivatives, for example 3-(4'-methyl)benzylidene-bornan-2-one, 3-benzylidene-bornan-2-one, N-[2(and 4)-2-oxyborn-3-ylidene-methyl)-benzyl]acrylamide polymer, 3-(4'-trimethylammonium)-benzylidene-bornan-2-one methyl sulfate, 3,3'-(1,4-phenylene-dimethine)-bis(7,7-dimethyl-2-oxo-bicyclo[2.2.1]heptane-1-methanesulfonic acid) and salts, 3-(4'-sulfo)benzylidene-bornan-2-one and salts; camphorbenzalkonium methosulfate;
phenyl-benzimidazole derivatives as disclosed in EP 1 167 358

TABLE 2

Suitable UV filter substances and adjuvants which can be additionally used with the UV absorbers (B) according to the present invention

| No. | Chemical Name | CAS No. |
|---|---|---|
| 1 | (+/−)-1,7,7-trimethyl-3-[(4-methylphenyl)methylene]bicyclo-[2.2.1]heptan-2-one; p-methyl benzylidene camphor | 36861-47-9 |
| 2 | 1,7,7-trimethyl-3-(phenylmethylene)bicyclo[2.2.1]heptan-2-one; benzylidene camphor | 15087-24-8 |
| 3 | (2-Hydroxy-4-methoxyphenyl)(4-methylphenyl)methanone | 1641-17-4 |
| 4 | 2,4-dihydroxybenzophenone | 131-56-6 |
| 5 | 2,2',4,4'-tetrahydroxybenzophenone | 131-55-5 |
| 6 | 2-Hydroxy-4-methoxy benzophenone; | 131-57-7 |
| 7 | 2-Hydroxy-4-methoxy benzophenone-5-sulfonic acid | 4065-45-6 |
| 8 | 2,2'-dihydroxy-4,4'-dimethoxybenzophenone | 131-54-4 |
| 9 | 2,2'-Dihydroxy-4-methoxybenzophenone | 131-53-3 |
| 10 | Alpha-(2-oxoborn-3-ylidene)toluene-4-sulphonic acid and its salts; Mexoryl SL | 56039-58-8 |
| 11 | 1-[4-(1,1-dimethylethyl)phenyl]-3-(4-methoxyphenyl)propane-1,3-dione; Avobenzone | 70356-09-1 |
| 12 | Methyl N,N,N-trimethyl-4-[(4,7,7-trimethyl-3-oxobicyclo[2,2,1]hept-2-ylidene)methyl]anilinium sulphate; Mexoryl SO | 52793-97-2 |
| 22 | 3,3,5-Trimethyl cyclohexyl-2-hydroxy benzoate; homosalate | 118-56-9 |
| 23 | Isopentyl p-methoxycinnamate; isoamyl methoxy cinnamate | 71617-10-2 |
| 27 | Menthyl-o-aminobenzoate | 134-09-8 |
| 28 | Menthyl salicylate | 89-46-3 |
| 29 | 2-Ethylhexyl 2-cyano,3,3-diphenylacrylate; Octocrylene | 6197-30-4 |
| 31 | 2-ethylhexyl 4-methoxycinnamate; Octyl Methoxy Cinnamate | 5466-77-3 |
| 32 | 2-ethylhexyl salicylate | 118-60-5 |
| 34 | 4-aminobenzoic acid | 150-13-0 |
| 35 | Benzoic acid, 4-amino-, ethyl ester, polymer with oxirane | 113010-52-9 |
| 38 | 2-phenyl-1H-benzimidazole-5-sulphonic acid; phenylbenzimidazolsulfonic acid | 27503-81-7 |
| 39 | 2-Propenamide, N-[[4-[(4,7,7-trimethyl-3-oxobicyclo[2.2.1]hept-2-ylidene)methyl]phenyl]methyl]-, homopolymer | 147897-12-9 |
| 40 | Triethanolamine salicylate | 2174-16-5 |
| 41 | 3,3'-(1,4-phenylenedimethylene)bis[7,7-dimethyl-2-oxo-bicyclo[2.2.1]heptane-1 methanesulfonic acid]; Cibafast H | 90457-82-2 |
| 42 | Titanium dioxide | 13463-67-7 |
| 44 | Zinc oxide | 1314-13-2 |
| 45 | 2,2'-Methylene-bis-[6-(2H-benzotriazol-2-yl)-4-(1,1,3,3-tetramethyl-butyl)-phenol]; Tinosorb M | 103597-45-1 |
| 46 | 1H-Benzimidazole-4,6-disulfonic acid, 2,2'-(1,4-phenylene)bis-, disodium salt | 180898-37-7 |
| 47 | Benzoic acid, 4,4'-[[6-[[4-[[(1,1-dimethylethyl)amino]carbonyl]phenyl]-amino]1,3,5-triazine-2,4-diyl]diimino]bis-, bis(2-ethylhexyl)ester; Diethylhexyl Butamido Triazone; Uvasorb HEB | 154702-15-5 |
| 48 | Phenol, 2-(2H-benzotriazol-2-yl)-4-methyl-6-[2-methyl-3-[1,3,3,3-tetramethyl-1-[(trimethylsilyl)oxy]disiloxanyl]propyl]-; Drometrizole Trisiloxane; Mexoryl XL | 155633-54-8 |
| 49 | Dimethicodiethylbenzalmalonate; Polysilicone 15; Parsol SLX | 207574-74-1 |
| 50 | Benzenesulfonic acid, 3-(2H-benzotriazol-2-yl)-4-hydroxy-5-(1-methyl-propyl)-, monosodium salt; Tinogard HS | 92484-48-5 |
| 52 | 1-Dodecanaminium, N-[3-[[4-(dimethylamino)benzoyl]amino]propyl]-N,N-dimethyl-, salt with 4-methylbenzenesulfonic acid (1:1); Escalol HP610 | 156679-41-3 |
| 53 | 1-Propanaminium, N,N,N-trimethyl-3-[(1-oxo-3-phenyl-2-propenyl)-amino]-, chloride | 177190-98-6 |
| 54 | 1H-Benzimidazole-4,6-disulfonic acid, 2,2'-(1,4-phenylene)bis- | 170864-82-1 |
| 57 | 1-Propanaminium, 3-[[3-[3-(2H-benzotriazol-2-yl)-5-(1,1-dimethyl-ethyl)-4-hydroxyphenyl]-1-oxopropyl]amino]-N,N-diethyl-N-methyl-, methyl sulfate (salt) | 340964-15-0 |
| 58 | 2-Propenoic acid, 3-(1H-imidazol-4-yl)- | 104-98-3 |
| 59 | Benzoic acid, 2-hydroxy-, [4-(1-methylethyl)phenyl]methyl ester | 94134-93-7 |
| 60 | 1,2,3-Propanetriol, 1-(4-aminobenzoate); glyceryl PABA | 136-44-7 |
| 61 | Benzeneacetic acid, 3,4-dimethoxy-a-oxo- | 4732-70-1 |
| 62 | 2-Propenoic acid, 2-cyano-3,3-diphenyl-, ethyl ester | 5232-99-5 |
| 63 | Anthralinic acid, p-menth-3-yl ester | 134-09-8 |
| 64 | 2,2'-bis(1,4-phenylene)-1H-benzimidazole-4,6-disulphonic acid mono-sodium salt or Disodium phenyl dibenzimidazole tetrasulfonate or Neo Heliopan AP | 349580-12-7, |
| 68 | sterols (cholesterol, lanosterol, phytosterols), as described in WO0341675 | |
| 69 | mycosporines and/or mycosporine-like amino acids as described in WO2002039974, e.g. Helioguard 365 from Milbelle AG, isolated mycosporine like amino acids from the red alga *porphyra umbilicalis* (INCI: *Porphyra Umbilicalis*) that are encapsulated into liposomes,) | |
| 70 | alpha-lipoic-acid as described in DE 10229995 | |
| 71 | synthetic organic polymers as described in EP 1371358, [0033]-[0041] | |
| 72 | phyllosilicates as described in EP 1371357 [0034]-[0037] | |

TABLE 2-continued

Suitable UV filter substances and adjuvants which can be additionally used with the UV absorbers (B) according to the present invention

| No. | Chemical Name | CAS No. |
|---|---|---|
| 73 | silica compounds as described in EP1371356, [0033]-[0041] | |
| 74 | inorganic particles as described in DE10138496 [0043]-[0055] | |
| 75 | latex particles as described in DE10138496 [0027]-[0040] | |
| 76 | 1H-Benzimidazole-4,6-disulfonic acid, 2,2'-(1,4-phenylene)bis-, disodium salt; Bisimidazylate; Neo Heliopan APC | 180898-37-7 |
| 81 | 2,4,6-Tris(p-biphenylyl)-s-triazine, Tinosorb A2B | 31274-51-8 |
| 82 | 2,4,6-Tris-1,1',4',1''-terphenyl-4-yl-1,3,5-triazine | |
| 83 | Di-2-ethylhexyl-3,5-dimethoxy-4-hydroxy-benzalmalonate (Oxynex ST, EMD Chemicals, as described in US 20040247536) | |

The cosmetic composition according to the present invention can be prepared by physically mixing the UV absorber(s) with the adjuvant using customary methods, for example by simply stirring together the individual components. The UV absorber can be used, for example, without further treatment, or in the micronized state, or in the form of a powder.

The cosmetic or pharmaceutical compositions/preparations according to the invention may also contain one or one more additional compounds as described below.

Fatty Alcohols

Guerbet alcohols based on fatty alcohols having from 6 to 18, preferably from 8 to 10 carbon atoms including cetyl alcohol, stearyl alcohol, cetearyl alcohol, oleyl alcohol, octyldodecanol, benzoate of $C_{12}$-$C_{15}$ alcohols, acetylated lanolin alcohol, etc.

Esters of Fatty Acids

Esters of linear $C_6$-$C_{24}$ fatty acids with linear $C_3$-$C_{24}$ alcohols, esters of branched $C_6$-$C_{13}$ carboxylic acids with linear $C_6$-$C_{24}$ fatty alcohols, esters of linear $C_6$-$C_{24}$ fatty acids with branched alcohols, especially 2-ethylhexanol, esters of hydroxycarboxylic acids with linear or branched $C_6$-$C_{22}$ fatty alcohols, especially dioctyl malates, esters of linear and/or branched fatty acids with polyhydric alcohols (for example propylene glycol, dimer diol or trimer trial) and/or Guerbet alcohols, for example caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselinic acid, linoleic acid, linolenic acid, elaeo-stearic acid, arachidic acid, gadoleic acid, behenic acid and erucic acid and technical-grade mixtures thereof (obtained, for example, in the pressure removal of natural fats and oils, in the reduction of aldehydes from Roelen's oxosynthesis or in the dimerisation of unsaturated fatty acids) with alcohols, for example, isopropyl alcohol, caproic alcohol, capryl alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linoyl alcohol, linolenyl alcohol, elaeostearyl alcohol, arachidyl alcohol, gadoleyl alcohol, behenyl alcohol, erucyl alcohol and brassidyl alcohol and technical-grade mixtures thereof (obtained, for example, in the high-pressure hydrogenation of technical-grade methyl esters based on fats and oils or aldehydes from Roelen's oxosynthesis and as monomer fractions in the dimerisation of unsaturated fatty alcohols).

Examples of such ester oils are isopropylmyristate, isopropylpalmitate, isopropylstearate, isopropyl isostearate, isopropyloleate, n-butylstearate, n-hexyllaurate, n-decyloleate, isooctyl-stearate, iso-nonylstearate, isononyl isononanoate, 2-ethylhexylpalmitate, 2-hexyllaurate, 2-hexyldecylstearate, 2-octyldodecylpalmitate, oleyloleate, oleylerucate, erucyloleate, erucyl-erucate, cetearyl octanoate, cetyl palmitate, cetyl stearate, cetyl oleate, cetyl behenate, cetyl acetate, myristyl myristate, myristyl behenate, myristyl oleate, myristyl stearate, myristyl palmitate, myristyl lactate, propylene glycol dicaprylate/caprate, stearyl heptanoate, diisostearyl malate, octyl hydroxystearate, etc.

Natural or Synthetic Tridycerides Including Glyceryl Esters and Derivatives

Di- or tri-glycerides, based on $C_6$-$C_8$ fatty acids, modified by reaction with other alcohols (caprylic/capric triglyceride, wheat germ glycerides, etc.). Fatty acid esters of polyglycerin (polyglyceryl-n such as polyglyceryl-4 caprate, polyglyceryl-2 isostearate, etc. or castor oil, hydrogenated vegetable oil, sweet almond oil, wheat germ oil, sesame oil, hydrogenated cottonseed oil, coconut oil, avocado oil, corn oil, hydrogenated castor oil, shea butter, cocoa butter, soybean oil, mink oil, sunflower oil, safflower oil, macadamia nut oil, olive oil, hydrogenated tallow, apricot kernel oil, hazelnut oil, borago oil, etc.

Waxes including esters of long-chain acids and alcohols as well as compounds having wax-like properties, e.g., carnauba wax, beeswax (white or yellow), lanolin wax, candellila wax, ozokerite, japan wax, paraffin wax, microcrystalline wax, ceresin, cetearyl esters wax, synthetic beeswax, etc. Also, hydrophilic waxes as Cetearyl Alcohol or partial glycerides.

Pearlescent Waxes:

Alkylene glycol esters, especially ethylene glycol distearate; fatty acid alkanolamides, especially coco fatty acid diethanolamide; partial glycerides, especially stearic acid monoglyceride; esters of polyvalent, unsubstituted or hydroxy-substituted carboxylic acids with fatty alcohols having from 6 to 22 carbon atoms, especially long-chained esters of tartaric acid; fatty substances, for example fatty alcohols, fatty ketones, fatty aldehydes, fatty ethers and fatty carbonates, which in total have at least 24 carbon atoms, especially laurone and distearyl ether; fatty acids, such as stearic acid, hydroxystearic acid or behenic acid, ring-opening products of olefin epoxides having from 12 to 22 carbon atoms with fatty alcohols having from 12 to 22 carbon atoms and/or polyols having from 2 to 15 carbon atoms and from 2 to 10 hydroxy groups, and mixtures thereof.

Hydrocarbon Oils:

Mineral oil (light or heavy), petrolatum (yellow or white), microcrystalline wax, paraffinic and isoparaffinic compounds, hydrogenated isoparaffinic molecules as polydecenes and polybutene, hydrogenated polyisobutene, squalane, isohexadecane, isododecane and others from plant and animal kingdom.

Silicones or Siloxanes (Organosubstituted Polysiloxanes)

Dimethylpolysiloxanes, methylphenylpolysiloxanes, cyclic silicones, and also amino-, fatty acid-, alcohol-, polyether-, epoxy-, fluorine-, glycoside- and/or alkyl-modified silicone compounds, which at room temperature may be in either liquid or resinous form. Linear polysiloxanes, dimethicone (Dow Corning 200 fluid, Rhodia Mirasil DM), dimethiconol, cyclic silicone fluids, cyclopentasiloxanes volatiles (Dow Corning 345 fluid), phenyltrimethicone (Dow Corning 556 fluid). Also suitable are simethicones, which are mixtures of dimethicones having an average chain length of from 200 to 300 dimethylsiloxane units with hydrogenated silicates. A detailed survey by Todd et al. of suitable volatile silicones may in addition be found in Cosm. Toil. 91, 27 (1976).

Fluorinated or Perfluorinated Oils

Perfluorhexane, dimethylcyclohexane, ethylcyclopentane, polyperfluoromethylisopropyl ether.

Emulsifiers

Any conventionally usable emulsifier can be used for the compositions. Emulsifier systems may comprise for example: carboxylic acids and their salts: alkaline soap of sodium, potassium and ammonium, metallic soap of calcium or magnesium, organic basis soap such as Lauric, palmitic, stearic and oleic acid etc . . . . Alkyl phosphates or phosphoric acid esters, acid phosphate, diethanolamine phosphate, potassium cetyl phosphate. Ethoxylated carboxylic acids or polyethyleneglycol esters, PEG-n acylates. Linear fatty alcohols having from 8 to 22 carbon atoms, branched from 2 to 30 mol of ethylene oxide and/or from 0 to 5 mol propylene oxide with fatty acids having from 12 to 22 carbon atoms and with alkylphenols having from 8 to 15 carbon atoms in the alkyl group. Fatty alcohol polyglycolether such as laureth-n, ceteareth-n, steareth-n, oleth-n. Fatty acid polyglycolether such as PEG-n stearate, PEG-n oleate, PEG-n cocoate. Monoglycerides and polyol esters. C12-C22 fatty acid mono- and di-esters of addition products of from 1 to 30 mol of ethylene oxide with polyols. Fatty acid and polyglycerol ester such as monostearate glycerol, diisostearoyl polyglyceryl-3-diisostearates, polyglyceryl-3-diisostearates, triglyceryl diisostearates, polyglyceryl-2-sesquiisostearates or polyglyceryl dimerates. Mixtures of compounds from a plurality of those substance classes are also suitable. Fatty acid polyglycolesters such as monostearate diethylene glycol, fatty acid and polyethylene glycol esters, fatty acid and saccharose esters such as sucro esters, glycerol and saccharose esters such as sucro glycerides. Sorbitol and sorbitan, sorbitan mono- and di-esters of saturated and unsaturated fatty acids having from 6 to 22 carbon atoms and ethylene oxide addition products. Polysorbate-n series, sorbitan esters such as sesquiisostearate, sorbitan, PEG-(6)-isostearate sorbitan, PEG-(10)-sorbitan laurate, PEG-17-dioleate sorbitan. Glucose derivatives, C8-C22 alkyl-mono and oligo-glycosides and ethoxylated analogues with glucose being preferred as the sugar component. O/W emulsifiers such as methyl gluceth-20 sesquistearate, sorbitan stearate/sucrose cocoate, methyl glucose sesquistearate, cetearyl alcohol/cetearyl glucoside. W/O emulsifiers such as methyl glucose dioleate/methyl glucose isostearate. Sulfates and sulfonated derivatives, dialkylsulfosuccinates, dioctyl succinate, alkyl lauryl sulfonate, linear sulfonated parafins, sulfonated tetraproplyne sulfonate, sodium lauryl sulfates, amonium and ethanolamine lauryl sulfates, lauyl ether sulfates, sodium laureth sulfates, sulfosuccinates, aceyl isothionates, alkanolamide sulfates, taurines, methyl taurines, imidazole sulfates. Amine derivatives, amine salts, ethoxylated amines, oxide amine with chains containning an heterocycle such as alkyl imidazolines, pyridine derivatives, isoquinoteines, cetyl pyridinium chlorure, cetyl pyridinium bromide, quaternary ammonium such as cetyltrimethylbroide amonium broide (CTBA), stearylalkonium; amide derivatives, alkanolamides such as acylamide DEA, ethoxylated amides such as PEG-n acylamide, oxydeamide; polysiloxane/-polyalkyl/polyether copolymers and derivatives, dimethicone, copolyols, silicone polyethylene oxide copolymer, silicone glycol copolymer; propoxylated or POE-n ethers (Meroxapols); polaxamers or poly(oxyethylene)m-block-poly(oxypropylene)n-block(oxyethylene); zwitterionic surfactants that carry at least one quaternary ammonium group and at least one carboxylate and/or sulfonate group in the molecule. Zwitterionic surfactants that are especially suitable are betaines, such as N-alkyl-N,N-dimethylammonium glycinates, cocoalkyldimethyl-ammonium glycinate, N-acylaminopropyl-N,N-dimethylammonium glycinates, cocoacylam inopropyldimethylammonium glycinate and 2-alkyl-3-carboxymethyl-3-hydroxyethylimidazolines each having from 8 to 18 carbon atoms in the alkyl or acyl group and also coco-acylaminoethylhydroxyethyl-carboxymethylglycinate, N-alkylbetaine, N-alkylamino-betaines. alkylimidazolines, alkylopeptides, lipoamino-acides, self emulsifying bases and the compounds as described in K. F. DePolo, A short textbook of cosmetology, Chapter 8, Table 8-7, p 250-251.

Non ionic emulsifiers such as PEG-6 beeswax (and) PEG-6 stearate (and) polyglyceryl-2-isostearate [Apifac], glyceryl stearate (and) PEG-100 stearate. [Arlacel 165], PEG-5 glyceryl stearate [arlatone 983 S], sorbitan oleate (and) polyglyceryl-3 ricinoleate. [Arlacel 1689], sorbitan stearate and sucrose cocoate [arlatone 2121], glyceryl stearate and laureth-23 [Cerasynth 945], cetearyl alcohol and ceteth-20 [Cetomacrogol Wax], cetearyl alcohol and colysorbate 60 and PEG-150 and stearate-20 [Polawax GP 200, Polawax NF], cetearyl alcohol and cetearyl polyglucoside [Emulgade PL 1618], cetearyl alcohol and ceteareth-20 [Emulgade 1000NI, Cosmowax], cetearyl alcohol and PEG-40 castor oil [Emulgade F Special], cetearyl alcohol and PEG-40 castor oil and sodium cetearyl sulfate [Emulgade F], stearyl alcohol and steareth-7 and steareth-10 [Emulgator E 2155], cetearyl alcohol and szeareth-7 and steareth-10 [Emulsifying wax U.S.N.F], glyceryl stearate and PEG-75 stearate [Gelot 64], propylene glycol ceteth-3 acetate. [Hetester PCS], propylene glycol isoceth-3 acetate [Hetester PHA], cetearyl alcohol and ceteth-12 and oleth-12 [Lanbritol Wax N 21], PEG-6 stearate and PEG-32 stearate [Tefose 1500], PEG-6 stearate and ceteth-20 and steareth-20 [Tefose 2000], PEG-6 stearate and ceteth-20 and glyceryl stearate and steareth-20 [Tefose 2561], glyceryl stearate and ceteareth-20 [Teginacid H, C, X]. Anionic emulsifiers such as PEG-2 stearate SE, glyceryl stearate SE [Monelgine, Cutina KD], propylene glycol stearate [Tegin P], cetearyl Alcohol and Sodium cetearyl sulfate [Lanette N, Cutina LE, Crodacol GP], cetearyl alcohol and sodium lauryl sulfate [Lanette W], trilaneth-4 phopshate and glycol stearate and PEG-2 stearate [Sedefos 75], glyceryl stearate and sodium lauryl Sulfate [Teginacid Special]. Cationic acid bases such as cetearyl alcohol and cetrimonium bromide.

The emulsifiers may be used in an amount of, for example, from 1 to 30% by weight, especially from 4 to 20% by weight and preferably from 5 to 10% by weight, based on the total weight of the composition.

When formulated in O/W emulsions, the preferably amount of such emulsifier system could represent 5% to 20% of the oil phase.

Adjuvants and Additives

The cosmetic/pharmaceutical preparations, for example creams, gels, lotions, alcoholic and aqueous/alcoholic solutions, emulsions, wax/fat compositions, stick preparations, powders or ointments, may in addition contain, as further adjuvants and additives, mild surfactants, super-fatting agents, consistency regulators, thickeners, polymers, stabilisers, biogenic active ingredients, deodorising active ingredients, anti-dandruff agents, film formers, swelling agents, further UV light-protective factors, antioxidants, hydrotropic agents, preservatives, insect repellents, self-tanning agents, solubilizers, perfume oils, colourants, bacteria-inhibiting agents and the like.

Super-Fatting Agents

Substances suitable for use as super-fatting agents are, for example, lanolin and lecithin and also polyethoxylated or acrylated lanolin and lecithin derivatives, polyol fatty acid esters, monoglycerides and fatty acid alkanolamides, the latter simultaneously acting as foam stabilisers.

Surfactants

Examples of suitable mild surfactants, that is to say surfactants especially well tolerated by the skin, include fatty alcohol polyglycol ether sulfates, monoglyceride sulfates, mono- and/or di-alkyl sulfosuccinates, fatty acid isethionates, fatty acid sarcosinates, fatty acid taurides, fatty acid glutamates, α-olefin sulfonates, ethercarboxylic acids, alkyl oligoglucosides, fatty acid glucamides, alkylamidobetaines and/or protein fatty acid condensation products, the latter preferably being based on wheat proteins.

Consistency Regulators/Thickners and Rheology Modifiers

Silicium dioxide, magnesium silicates, aluminium silicates, polysaccharides or derivatives thereof for example hyaluronic acid, xanthan gum, guar-guar, agar-agar, alginates, carraghenan, gellan, pectines, or modified cellulose such as hydroxycellulose, hydroxypropyl-methylcellulose. In addition polyacrylates or homopolymer of reticulated acrylic acids and polyacrylamides, carbomer (carbopol types 980, 981, 1382, ETD 2001, ETD2020, Ultrez 10) or Salcare range such as Salcare SC80 (steareth-10 allyl ether/acrylates copolymer), Salcare SC81 (acrylates copolymer), Salcare SC91 and Salcare AST (sodium acrylates copolymer/PPG-1 trideceth-6), sepigel 305 (polyacrylamide/laureth-7), Simulgel NS and Simulgel EG (hydroxyethyl acrylate/sodium acryloyldimethyl taurate copolymer), Stabilen 30 (acrylates/vinyl isodecanoate crosspolymer), Pemulen TR-1 (acrylates/C10-30 alkyl acrylate crosspolymer), Luvigel EM (sodium acrylates copolymer), Aculyn 28 (acrylates/beheneth-25 methacrylate copolymer), etc.

Polymers

Suitable cationic polymers are, for example, cationic cellulose derivatives, for example a quaternised hydroxymethyl cellulose obtainable under the name Polymer JR 400 from Amerchol, cationic starches, copolymers of diallylammonium salts and acrylam ides, quaternised vinyl-pyrrolidone/vinyl imidazole polymers, for example Luviquat® (BASF), condensation products of polyglycols and amines, quaternised collagen polypeptides, for example lauryldimonium hydroxypropyl hydrolyzed collagen (Lamequat®L/Grunau), quaternised wheat polypeptides, polyethyleneimine, cationic silicone polymers, for example amidomethicones, copolymers of adipic acid and dimethylaminohydroxypropyldiethylenetriamine (Cartaretin/Sandoz), copolymers of acrylic acid with dimethyldiallylammonium chloride (Merquat 550/Chemviron), polyaminopolyamides, as described, for example, in FR-A-2 252 840, and the crosslinked water-soluble polymers thereof, cationic chitin derivatives, for example of quaternised chitosan, optionally distributed as microcrystals; condensation products of dihaloalkyls, for example dibromobutane, with bisdialkylamines, for example bisdimethylamino-1,3-propane, cationic guar gum, for example Jaguar C-17, Jaguar C-16 from Celanese, quaternised ammonium salt polymers, for example Mirapol A-15, Mirapol AD-1, Mirapol AZ-1 from Miranol. As anionic, zwitterionic, amphoteric and non-ionic polymers there come into consideration, for example, vinyl acetate/crotonic acid copolymers, vinylpyrrolidone/vinyl acrylate copolymers, vinyl acetate/butyl maleate/isobornyl acrylate copolymers, methyl vinyl ether/maleic anhydride copolymers and esters thereof, uncrosslinked polyacrylic acids and polyacrylic acids crosslinked with polyols, acrylamidopropyl-trimethylammonium chloride/acrylate copolymers, octyl acrylamide/methyl methacrylatetert-butylaminoethyl methacrylate/2-hydroxypropyl methacrylate copolymers, polyvinylpyrrolidone, vinylpyrrolidone/vinyl acetate copolymers, vinylpyrrolidone/dimethylaminoethyl methacrylate/vinyl caprolactam terpolymers and also optionally derivatised cellulose ethers and silicones. Furthermore the polymers as described in EP 1093796 (pages 3-8, paragraphs 17-68) may be used.

Biogenic Active Ingredients

Biogenic active ingredients are to be understood as meaning, for example, tocopherol, tocopherol acetate, tocopherol palmitate, ascorbic acid, deoxyribonucleic acid, retinol, bisabolol, allantoin, phytantriol, panthenol, AHA acids, amino acids, ceramides, pseudoceramides, essential oils, plant extracts and vitamin complexes.

Deodorising Active Ingredients

As deodorising active ingredients there come into consideration, for example, antiperspirants, for example aluminium chlorohydrates (see J. Soc. Cosm. Chem. 24, 281 (1973)). Under the trade mark Locron® of Hoechst AG, Frankfurt (FRG), there is available comercially, for example, an aluminium chlorohydrate corresponding to formula $Al_2(OH)_5Cl \times 2.5H_2O$, the use of which is especially preferred (see J. Pharm. Pharmacol. 26, 531 (1975)). Besides the chlorohydrates, it is also possible to use aluminium hydroxyacetates and acidic aluminium/zirconium salts. Esterase inhibitors may be added as further deodorising active ingredients. Such inhibitors are preferably trialkyl citrates, such as trimethyl citrate, tripropyl citrate, triisopropyl citrate, tributyl citrate and especially triethyl citrate (Hydagen CAT, Henkel), which inhibit enzyme activity and hence reduce odour formation. Further substances that come into consideration as esterase inhibitors are sterol sulfates or phosphates, for example lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester and hydroxycarboxylic acids and esters thereof, for example citric acid, malic acid, tartaric acid or tartaric acid diethyl ester. Antibacterial active ingredients that influence the germ flora and kill or inhibit the growth of sweat-decomposing bacteria can likewise be present in the preparations (especially in stick preparations). Examples include chitosan, phenoxyethanol and chlorhexidine gluconate, 5-(Triclosan, Irgasan, Ciba Specialty Chemicals Inc.) has also proved especially effective.

Anti-Dandruff Agents

As anti-dandruff agents there may be used, for example, climbazole, octopirox and zinc pyrithione. Customary film formers include, for example, chitosan, microcrystalline chitosan, quaternised chitosan, polyvinylpyrrolidone, vinylpyrrolidone/vinyl acetate copolymers, polymers of quaternary cellulose derivatives containing a high proportion of acrylic acid, collagen, hyaluronic acid and salts thereof and similar compounds.

Antioxidants

In addition to the primary light-protective substances it is also possible to use secondary light-protective substances of the antioxidant kind that interrupt the photochemical reaction chain triggered when UV radiation penetrates the skin or hair. Typical examples of such antioxidants are amino acids (e.g. glycine, histidine, tyrosine, tryptophan) and derivatives thereof, imidazoles (e.g. urocanic acid) and derivatives thereof, peptides, such as D,L-carnosine, D-carnosine, L-carnosine and derivatives thereof (e.g. anserine), carotinoids, carotenes, lycopene and derivatives thereof, chlorogenic acid and derivatives thereof, lipoic acid and derivatives thereof (e.g. dihydrolipoic acid), aurothioglycose, propylthiouracil and other thiols (e.g. thioredoxin, glutathione, cysteine, cystine, cystamine and the glycosyl, N-acetyl, methyl, ethyl, propyl, amyl, butyl, lauryl, palmitoyl, oleyl, linoleyl, cholesteryl and glyceryl esters thereof) and also salts thereof, dilauryl thiodipropionate, distearyl thiodipropionate, thiodi-propionic acid and derivatives thereof (esters, ethers, peptides, lipids, nucleotides, nucleosides and salts) and also sulfoximine compounds (e.g. buthionine sulfoximines, homocysteine sulfoximine, buthionine sulfones, penta-, hexa-, hepta-thionine sulfoximine), also (metal) chelating agents (e.g. hydroxy fatty acids, palmitic acid phytic acid, lactoferrin), hydroxy acids (e.g. citric acid, lactic acid, malic acid), humic acid, bile acid, bile extracts, bilirubin, biliverdin, EDTA, EDDS, EGTA and derivatives thereof, unsaturated fatty acids and derivatives thereof (e.g. linolenic acid, linoleic acid, oleic acid), folic acid and derivatives thereof, ubiquinone and ubiquinol and derivatives thereof, vitamin C and derivatives (e.g. ascorbyl palmitate, magnesium ascorbyl phosphate, ascorbyl acetate), tocopherols and derivatives (e.g. vitamin E acetate), vitamin A and derivatives (e.g. vitamin A palmitate) and also coniferyl benzoate of benzoin resin, rutinic acid and derivatives thereof, glycosylrutin, ferulic acid, furfurylidene glucitol, carnosine, butyl hydroxytoluene, butyl hydroxyanisole, nordihydroguaiaretic acid, trihydroxybutyrophenone, uric acid and derivatives thereof, mannose and derivatives thereof, superoxide dismutase, N-[3-(3,5-di-tert-butyl-4-hydroxyphenyl)propionyl]sulfanilic acid (and salts thereof, for example the disodium salts), zinc and derivatives thereof (e.g. ZnO, $ZnSO_4$), selenium and derivatives thereof (e.g. selenium methionine), stilbene and derivatives thereof (e.g. stilbene oxide, trans-stilbene oxide) and the derivatives suitable according to the invention (salts, esters, ethers, sugars, nucleotides, nucleosides, peptides and lipids) of those mentioned active ingredients. HALS (="Hindered Amine Light Stabilizers") compounds may also be mentioned.

Further synthetic and natural antioxidants are listed e.g. in patent WO 0025731: Structures 1-3 (page 2), structure 4 (page 6), structures 5-6 (page 7) and compounds 7-33 (page 8-14).

Hydrotropic Agents

To improve the flow behaviour it is also possible to employ hydrotropic agents, for example ethoxylated or non ethoxylated mono-alcohols, diols or polyols with a low number of carbon atoms or their ethers (e.g. ethanol, isopropanol, 1,2-dipropanediol, propyleneglycol, glyerin, ethylene glycol, ethylene glycol monoethylether, ethylene glycol monobutylether, propylene glycol monomethylether, propylene glycol monoethylether, propylene glycol monobutylether, diethylene glycol monomethylether; diethylene glycol monoethylether, diethylene glycol monobutylether and similar products). The polyols that come into consideration for that purpose have preferably from 2 to 15 carbon atoms and at least two hydroxy groups. The polyols may also contain further functional groups, especially amino groups, and/or may be modified with nitrogen. Typical examples are as follows: glycerol, alkylene glycols, for example ethylene glycol, diethylene glycol, propylene glycol, butylene glycol, hexylene glycol and also polyethylene glycols having an average molecular weight of from 100 to 1000 Dalton; technical oligoglycerol mixtures having an intrinsic degree of condensation of from 1.5 to 10, for example technical diglycerol mixtures having a diglycerol content of from 40 to 50% by weight; methylol compounds, such as, especially, trimethylolethane, trimethylolpropane, trimethylolbutane, pentaerythritol and dipentaerythritol; lower alkyl-glucosides, especially those having from 1 to 8 carbon atoms in the alkyl radical, for example methyl and butyl glucoside; sugar alcohols having from 5 to 12 carbon atoms, for example sorbitol or mannitol; sugars having from 5 to 12 carbon atoms, for example glucose or saccharose; amino sugars, for example glucamine; dialcohol amines, such as diethanolamine or 2-amino-1,3-propanediol.

Preservatives and Bacteria-Inhibiting Agents

Suitable preservatives include, for example, Methyl-, Ethyl-, Propyl-, Butyl-parabens, Benzalkonium chloride, 2-Bromo-2-nitro-propane-1,3-diol, Dehydroacetic acid, Diazolidinyl Urea, 2-Dichloro-benzyl alcohol, DMDM hydantoin, Formaldehyde solution, Methyldibromoglutanitrile, Phenoxyethanol, Sodium Hydroxymethylglycinate, Imidazolidinyl Urea, Triclosan and further substance classes listed in the following reference: K. F. DePolo—A short textbook of cosmetology, Chapter 7, Table 7-2, 7-3, 7-4 and 7-5, p 210-219.

Typical examples of bacteria-inhibiting agents are preservatives that have a specific action to against gram-positive bacteria, such as 2,4,4'-trichloro-2'-hydroxydiphenyl ether, chlorhexidine (1,6-di(4-chlorophenyl-biguanido)hexane) or TCC (3,4,4'-trichlorocarbanilide). A large number of aromatic substances and ethereal oils also have antimicrobial properties. Typical examples are the active ingredients eugenol, menthol and thymol in clove oil, mint oil and thyme oil. A natural deodorising agent of interest is the terpene alcohol farnesol (3,7,11-trimethyl-2,6,10-dodecatrien-1-ol), which is present in lime blossom oil. Glycerol monolaurate has also proved to be a bacteriostatic agent. The amount of the additional bacteria-inhibiting agents present is usually from 0.1 to 2% by weight, based on the solids content of the preparations.

Perfume Oils

There may be mentioned as perfume oils mixtures of natural and/or synthetic aromatic substances. Natural aromatic substances are, for example, extracts from blossom (lilies, lavender, roses, jasmine, neroli, ylang-ylang), from stems and leaves (geranium, patchouli, petitgrain), from fruit (aniseed, coriander, carraway, juniper), from fruit peel (bergamot, lemons, oranges), from roots (mace, angelica, celery, cardamom, costus, iris, calmus), from wood (pinewood, sandalwood, guaiacum wood, cedarwood, rosewood), from herbs and grasses (tarragon, lemon grass, sage, thyme), from needles and twigs (spruce, pine, Scots pine, mountain pine), from resins and balsams (galbanum, elemi, benzoin, myrrh, olibanum, opoponax). Animal raw materials also come into consideration, for example civet and castoreum. Typical synthetic aromatic substances are, for example, products of the ester, ether, aldehyde, ketone, alcohol or hydrocarbon type. Aromatic substance compounds of the ester type are, for example, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethylmethylphenyl glycinate, allylcyclohexyl propionate, styrallyl propionate and benzyl salicylate. The ethers include, for example, benzyl ethyl ether; the aldehydes include, for example, the linear alkanals having from 8 to 18 hydrocarbon atoms, citral, citronellal, citronellyl oxyacetaldehyde, cyclamen aldehyde, hydroxycitronellal, lilial and bourgeonal; the ketones include, for example, the ionones, isomethylionone and methyl cedryl ketone; the alcohols include, for example, anethol, citronellol, eugenol, isoeugenol, geraniol, linalool, phenyl ethyl alcohol and terpinol; and the hydrocarbons include mainly the terpenes and balsams. It is preferable, however, to use mixtures of various aromatic substances that together produce an attractive scent. Ethereal oils of relatively low volatility, which are chiefly used as aroma components, are also suitable as perfume oils, e.g. sage oil, camomile oil, clove oil, melissa oil, oil of cinnamon leaves, lime blossom oil, juniper berry oil, vetiver oil, olibanum oil, galbanum oil, labolanum oil and lavandin oil. Preference is given to the use of bergamot oil, dihydromyrcenol, lilial, lyral, citronellol, phenyl ethyl alcohol, hexyl cinnamaldehyde, geraniol, benzyl acetone, cyclamen aldehyde, linalool, boisambrene forte, ambroxan, indole, hedione, sandelice, lemon oil, tangerine oil, orange oil, allyl amyl glycolate, cyclovertal, lavandin oil, muscatel sage oil, damascone, bourbon geranium oil, cyclohexyl salicylate, vertofix coeur, iso-E-Super, Fixolide NP, evernyl, iraldein gamma, phenylacetic acid, geranyl acetate, benzyl acetate, rose oxide, romillat, irotyl and floramat alone or in admixture with one another.

Colourants

As colourants substances may be used that are suitable and permitted for cosmetic purposes, as compiled, for example, in the publication "Kosmetische Färbemittel" of the Farb-stoffkommission der Deutschen Forschungsgemeinschaft, Verlag Chemie, Weinheim, 1984, pages 81 to 106. The colourants are usually used in concentrations of from 0.001 to 0.1% by weight, based on the total mixture.

Other Adjuvants

It is furthermore possible for the cosmetic preparations to contain, as adjuvants, anti-foams, such as silicones, structurants, such as maleic acid, solubilizers, such as ethylene glycol, propylene glycol, glycerol or diethylene glycol, opacifiers, such as latex, styrene/PVP or styrene/acrylamide copolymers, complexing agents, such as EDTA, NTA, alaninediacetic acid or phosphonic acids, propellants, such as propane/butane mixtures, $N_2O$, dimethyl ether, $CO_2$, $N_2$ or air, so-called coupler and developer components as oxidation dye precursors, reducing agents, such as thioglycolic acid and derivatives thereof, thiolactic acid, cysteamine, thiomalic acid or mercaptoethanesulfonic acid, or oxidising agents, such as hydrogen peroxide, potassium bromate or sodium bromate.

Suitable insect repellents are, for example, N,N-diethyl-m-toluamide, 1,2-pentanediol or insect repellent 3535; suitable self-tanning agents are, for example, dihydroxyacetone and/or erythrulose or dihydroxy acetone and/or dihydroxy acetone precursors as described in WO 01/85124 and/or erythrulose.

Polymeric Beads or Hollow Spheres as SPF Enhancers

The combination of the UV-absorbers and UV-absorber combinations, listed above, with SPF enhancers, such as non-active ingredients like Styrene/acrylates copolymer, silica beads, spheroidal magnesium silicate, crosslinked Polymethylmethacrylates (PMMA; Micopearl M305 Seppic), can maximize better the UV protection of the sun products. Holosphere additives (Sunspheres® ISP, Silica Shells Kobo.) deflect radiation and the effective path length of the photon is therefore increased. (EP0893119). Some beads, as mentioned previously, provide a soft feel during spreading. Moreover, the optical activity of such beads, e.g. Micropearl M305, cans modulate skin shine by eliminating reflection phenomena and indirectly may scatter the UV light.

Cosmetic or Pharmaceutical Preparations

Cosmetic or pharmaceutical formulations are contained in a wide variety of cosmetic preparations. There come into consideration, for example, especially the following preparations:

skin-care preparations, e.g. skin-washing and cleansing preparations in the form of tablet-form or liquid soaps, soapless detergents or washing pastes, bath preparations, e.g. liquid (foam baths, milks, shower preparations) or solid bath preparations, e.g. bath cubes and bath salts;

skin-care preparations, e.g. skin emulsions, multi-emulsions or skin oils;

cosmetic personal care preparations, e.g. facial make-up in the form of day creams or powder creams, face powder (loose or pressed), rouge or cream make-up, eye-care preparations, e.g. eyeshadow preparations, mascara, eyeliner, eye creams or eye-fix creams; lip-care preparations, e.g. lipsticks, lip gloss, lip contour pencils, nail-care preparations, such as nail varnish, nail varnish removers, nail hardeners or cuticle removers;

foot-care preparations, e.g. foot baths, foot powders, foot creams or foot balsams, special deodorants and antiperspirants or callus-removing preparations;

light-protective preparations, such as sun milks, lotions, creams or oils, sunblocks or tropicals, pre-tanning preparations or after-sun preparations;

skin-tanning preparations, e.g. self-tanning creams;

depigmenting preparations, e.g. preparations for bleaching the skin or skin-lightening preparations;

insect-repellents, e.g. insect-repellent oils, lotions, sprays or sticks;

deodorants, such as deodorant sprays, pump-action sprays, deodorant gels, sticks or roll-ons;

antiperspirants, e.g. antiperspirant sticks, creams or roll-ons;

preparations for cleansing and caring for blemished skin, e.g. synthetic detergents (solid or liquid), peeling or scrub preparations or peeling masks;

hair-removal preparations in chemical form (depilation), e.g. hair-removing powders, liquid hair-removing preparations, cream- or paste-form hair-removing preparations, hair-removing preparations in gel form or aerosol foams;

shaving preparations, e.g. shaving soap, foaming shaving creams, non-foaming shaving creams, foams and gels, preshave preparations for dry shaving, aftershaves or aftershave lotions;

fragrance preparations, e.g. fragrances (eau de Cologne, eau de toilette, eau de parfum, parfum de toilette, perfume), perfume oils or perfume creams;

cosmetic hair-treatment preparations, e.g. hair-washing preparations in the form of shampoos and conditioners, hair-care preparations, e.g. pre-treatments preparations, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, hair foams, hairsprays, bleaching preparations, e.g. hydrogen peroxide solutions, lightening shampoos, bleaching creams, bleaching powders, bleaching pastes or oils, temporary, semi-permanent or permanent hair colourants, preparations containing self-oxidising dyes, or natural hair colourants, such as henna or camomile.

Presentation Forms

The final formulations listed may exist in a wide variety of presentation forms, for example:
- in the form of liquid preparations as a W/O, O/W, O/W/O, W/O/W or PIT emulsion and all kinds of microemulsions,
- in the form of a gel,
- in the form of an oil, a cream, milk or lotion,
- in the form of a powder, a lacquer, a tablet or make-up,
- in the form of a stick,
- in the form of a spray (spray with propellant gas or pump-action spray) or an aerosol,
- in the form of a foam, or
- in the form of a paste.

Of special importance as cosmetic preparations for the skin are light-protective preparations, such as sun milks, lotions, creams, oils, sunblocks or tropicals, pretanning preparations or after-sun preparations, also skin-tanning preparations, for example self-tanning creams. Of particular interest are sun protection creams, sun protection lotions, sun protection milks and sun protection preparations in the form of a spray.

Of special importance as cosmetic preparations for the hair are the above-mentioned preparations for hair treatment, especially hair-washing preparations in the form of shampoos, hair conditioners, hair-care preparations, e.g. pre-treatment preparations, hair tonics, styling creams, styling gels, pomades, hair rinses, treatment packs, intensive hair treatments, hair-straightening preparations, liquid hair-setting preparations, hair foams and hairsprays. Of special interest are hair-washing preparations in the form of shampoos.

A shampoo has, for example, the following composition: from 0.01 to 5% by weight of a UV absorber according to the invention, 12.0% by weight of sodium laureth-2-sulfate, 4.0% by weight of cocamidopropyl betaine, 3.0% by weight of sodium chloride, and water ad 100%.

For example, especially the following hair-cosmetic formulations may be used:

$a_1$) spontaneously emulsifying stock formulation, consisting of the UV absorber according to the invention, PEG-6-$C_{10}$oxoalcohol and sorbitan sesquioleate, to which water and any desired quaternary ammonium compound, for example 4% minkamidopropyl dimethyl-2-hydroxyethyl-ammonium chloride or Quaternium 80 is added;

$a_2$) spontaneously emulsifying stock formulation consisting of the UV absorber according to the invention, tributyl citrate and PEG-20-sorbitan monooleate, to which water and any desired quaternary ammonium compound, for example 4% Aminkamidopropyl dimethyl-2-hydroxyethylammonium chloride or Quaternium 80 is added;

b) quat-doped solutions of the UV absorber according to the invention in butyl triglycol and tributyl citrate;

c) mixtures or solutions of the UV absorber according to the invention with n-alkylpyrrolidone.

The cosmetic preparation according to the invention is distinguished by excellent protection of human skin against the damaging effect of sunlight.

Solubility Tests

EXPERIMENTAL 2 ml of the solubilizing agent are filled into a 20 ml vial with cap. Afterwards 0.02 g (1%) of the respective substance (UV Filter) are weighed and added to the solvent. The vial is placed into a thermostat-controlled water bath, wherein the suspension/solution is stirred during seven days at 25° C.

If the amount of substance put into the solubilizing agent is fully soluble, additional substance is added until precipitation can be observed.

After seven days, the sample is centrifuged for 30 minutes at 13000 rpm at 25° C. The supernatant is transferred into a small beaker. In case the sample is still turbid, it is filtered through a 0.2 μm non-steril Membrex 25 PET filter. Clear solutions must not be filtered. When a clear solution is obtained, the concentration of the substance is determined with UV/Vis-spectrometry. For this purpose the sample may be diluted with a suitable solvent or, in case of lower concentrations, may be measured as is.

In order to evaluate the concentration from the UV-spectroscopic results, the extinction coefficient is needed, which is determined independently with a solvent of similar polarity like that one used for dilution of the saturated solutions.

The solubility can be calculated using the equation of the Lambert-Beer-Law.

Test Results:

| UV filter compound of formula | (TAT-02) | (HTP-02) | (BPH-02) |
|---|---|---|---|
| morpholine amide o formula (AM-01) | 45% | 15% | >40% |

| | | | Example | | | |
|---|---|---|---|---|---|---|
| Water Resistant Sunscreen, W/O, SPF 50, UVA-PF/SPF > 1/3 | | | B-00 | B-01 | B-02 | B-03 |
| Composition | Trade Name | INCI-Name | % (w/w) as supplied | % (w/w) as supplied | % (w/w) as supplied | % (w/w) as supplied |
| Part A | Dehymuls ® LE | PEG-30 Dipolyhydroxystearate | 3.50 | 3.50 | 3.50 | 3.50 |
| | Abil EM 90 | Cetyl PEG/PPG-10/1 Dimethicone | 1.00 | 1.00 | 1.00 | 1.00 |
| | DUB DIBA | Disobutyl Adipate | 5.00 | | 5.00 | 5.00 |

-continued

| | | | | | | |
|---|---|---|---|---|---|---|
| | Cetiol ® AB | C12-15 Alkyl Benzoate | 5.00 | 5.00 | | 5.00 |
| | Arlamol HD | Isohexadecane | 3.00 | 3.00 | 3.00 | |
| | Magnesium Stearate | Magnesium Stearate | 1.50 | 1.50 | 1.50 | 1.50 |
| | Uvinul ® MC 80 | Ethylhexyl Methoxy-cinnamate | 10.00 | 10.00 | 10.00 | 10.00 |
| | Uvinul ® A Plus | Diethylamino Hydroxy-benzoyl Hexyl Benzoate | 10.00 | 10.00 | 10.00 | 10.00 |
| | Uvinul ® T150 | Ethylhexyl Triazone | 2.50 | 2.50 | 2.50 | 2.50 |
| | Tinosorb ® S | Bis-Ethylhexyloxy-phenol Methoxypheyl Triazine | 2.20 | 2.20 | 2.20 | 2.20 |
| | Compound of formula (AM-01) | | | 5.00 | 5.00 | 3.00 |
| Part B | Water, demin. | Aqua | Qs to 100 | Qs to 100 | Qs to 100 | Qs to 100 |
| | Glycerin | Glycerin | 3.00 | 3.00 | 3.00 | 3.00 |
| | Magnesium Sulfate Heptahydrate | Magnesium Sulfate | 1.00 | 1.00 | 1.00 | 1.00 |
| Part C | Xiameter PMX-0345 Cyclosiloxane | Cyclopentasiloxane, Cyclohexasiloxane | 5.00 | 5.00 | 5.00 | 5.00 |
| | Preservative | Phenoxyethanol | 1.00 | 1.00 | 1.00 | 1.00 |

| | | | Example | | | |
|---|---|---|---|---|---|---|
| la Boite de Pandore Sun Care Cream SPF 30 | | | B-04 | B-05 | B-06 | B-07 |
| Composition | Trade Name | INCI-Name | % (w/w) as supplied | % (w/w) as supplied | % (w/w) as supplied | % (w/w) as supplied |
| Part A | Eumulgin ® SG | Sodium Stearoyl Glutamate | 2.00 | 2.00 | 2.00 | 2.00 |
| | Lanette ® 18 | Stearyl Alcohol | 1.00 | 1.00 | 1.00 | 1.00 |
| | Tegosoft XC | Phenoxyethyl Caprylate | | 8.00 | 8.00 | 8.00 |
| | Cetiol ® B | Dibutyl Adipate | 5.00 | | 5.00 | 5.00 |
| | Finsolv EB | Ethylhexyl Benzoate | 5.00 | 5.00 | | 5.00 |
| | Crodamol LL | Lauryl Lactate | 3.00 | 3.00 | 3.00 | |
| | Uvinul ® A Plus | Diethylamino Hydroxybenzoyl Hexyl Benzoate | 10.00 | 10.00 | 10.00 | 10.00 |
| | Uvinul ® T 150 | Ethylhexyl Triazone | 3.00 | 3.00 | 3.00 | 3.00 |
| | Tinosorb ® S | Bis-Ethyl-hexyloxyphenol Methoxyphenyl Triazine | 3.00 | 3.00 | 3.00 | 3.00 |
| | Compound of formula (AM-01) | | 8.00 | 5.00 | 5.00 | 3.00 |
| Part B | Water, demin. | Aqua | Qs to 100 | Qs to 100 | Qs to 100 | Qs to 100 |
| | Glycerin | Glycerin | 3.00 | 3.00 | 3.00 | 3.00 |
| | Cosmedia ® SP | Sodium Polyacrylate | 0.60 | 0.60 | 0.60 | 0.60 |
| | Keltrol CG-RD | Xantham Gum | 0.50 | 0.50 | 0.50 | 0.50 |
| | Edeta ® BD | Disodium EDTA | 0.20 | 0.20 | 0.20 | 0.20 |
| Part C | Orgasol Caresse | Polyamide-5 | 1.50 | 1.50 | 1.50 | 1.50 |
| | Protectol PE | Phenoxyethanol | 1.00 | 1.00 | 1.00 | 1.00 |

Manufacturing Instruction:

Heat up phase A and B to 80° C.

Add phase B slowly into phase A under increased stirring speed.

Homogenize for a short time.

Cool down under gentle stirring. Below 40° C. add phase C.

Finally homogenize for a short time again.

Specifications

Viscosity: 4000-7000 mPas (Brookfield; DV-III+; spindle LV2; 20 rpm; 20° C.)

SPF in vitro: 50.9

| | | | Example B-08 |
|---|---|---|---|
| UV Expert Summer Passion Milk SPF 50+ | | | |
| Composition | Trade Name | INCI-Name | % (w/w) as supplied |
| Part A | Eumulgin ® SG | Sodium Stearoyl Glutamate | 2.00 |
| | Lanette ® 18 | Stearyl Alcohol | 1.00 |
| | Cetiol ® B | Dibutyl Adipate | 4.00 |
| | Uvinul ® A Plus | Diethylamino Hydroxybenzoyl Hexyl Benzoate | 7.00 |
| | Uvinul ® T 150 | Ethylhexyl Triazone | 3.00 |
| | Tinosorb ® S | Bis-Ethylhexyloxyphenol Methoxyphenyl Triazine | 4.00 |
| | Compound of formula (AM-01) | | 14.00 |

-continued

| UV Expert Summer Passion Milk SPF 50+ | | | Example B-08 |
|---|---|---|---|
| Composition | Trade Name | INCI-Name | % (w/w) as supplied |
| Part B | Water, demin. | Aqua | 50.80 |
| | Rheocare ® XG | Xanthan Gum | 0.50 |
| | Edeta ® BD | Disodium EDTA | 0.20 |
| Part C | Water, demin. | Aqua | 10.00 |
| | Eusolex 232 | Phenylbenzimidazole Sulfonic Acid | 3.50 |
| | Tris Amino Ultra Pur | Trometamine | qs |

Manufacturing Instruction:
Heat up phase B without Rheocare XG.
Heat up phase A to 75° C. under stirring.
At 75° C. add Rheocare XG to phase B under homogenizer.
Add phase A into B under stirring, homogenize.
Cool down to room temperature under continuous stirring, then add phase C previously mixed. Adjust pH value to at least 7.
Specifications
Viscosity: 5500-7000 mPas (Brookfield; DV-III+; spindle LV2; 20 rpm; 20° C.)
SPF in vitro: 63

The invention claimed is:

1. A skin care composition comprising
(A) a solubilizing agent according to formula

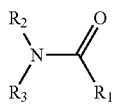

(1)

wherein
$R_1$ represents $C_6$-$C_{24}$ alkyl;
$R_2$ and $R_3$ together with the linking nitrogen atom form a 5 or 6 membered heteroaromatic radical which optionally contains one or more nitrogen atoms and said heteroaromatic radical is optionally substituted only by one or more $C_1$-$C_4$ alkyl, and
(B) at least one organic UV filter;
wherein when formula 1 is a 6 membered ring, the at least one organic UV filter is selected from the group consisting of
(B1) benzophenone derivatives,
(B2) hydroxyphenyl triazine derivatives; and
(B3) trianilino-s-triazine derivatives;
and
wherein when formula 1 is a 5 membered ring, the at least one organic UV filter is selected from the group consisting of
(B2) hydroxyphenyl triazine derivatives and
(B3) trianilino-s-triazine derivatives.

2. The composition according to claim 1, wherein in formula (1) $R_1$ is $C_6$-$C_{15}$alkyl.

3. The composition according to claim 1, wherein in formula (1) $R_1$ is n-heptyl.

4. The composition according to claim 1, wherein in formula (1) $R_1$ is n-nonyl.

5. The composition according to claim 1, wherein in formula (1) $R_1$ is n-undecyl.

6. The composition according to claim 1, wherein the organic UV filters (B) are present in admixtures of at least two different UV filters.

7. The composition according to claim 1, wherein the benzophenone derivatives (B1) correspond to the formula

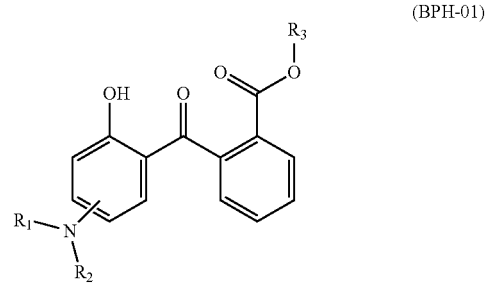

(BPH-01)

wherein
$R_1$ and $R_2$ independently from each other are hydrogen; $C_1$-$C_{20}$alkyl; $C_3$-$C_{10}$cycloalkyl; or $C_3$-$C_{10}$cycloalkenyl, wherein the radicals $R_1$ and $R_2$ together with the nitrogen atom, to which they are bonded, may form a 5- or 6-membered ring; and
$R_3$ is $C_1$-$C_{20}$alkyl.

8. The composition according to claim 1, wherein the benzophenone derivatives (B1) correspond to the formula

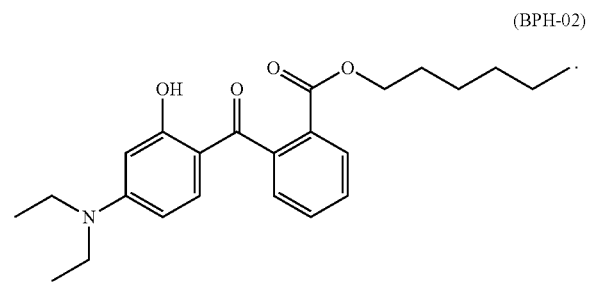 [SMILES: CCCCCCOC(=O)c1ccccc1C(=O)c1ccc(N(CC)CC)cc1O]

(BPH-02)

9. The composition according to claim 1, wherein the hydroxyphenyl triazine derivatives (B2) correspond to the formula

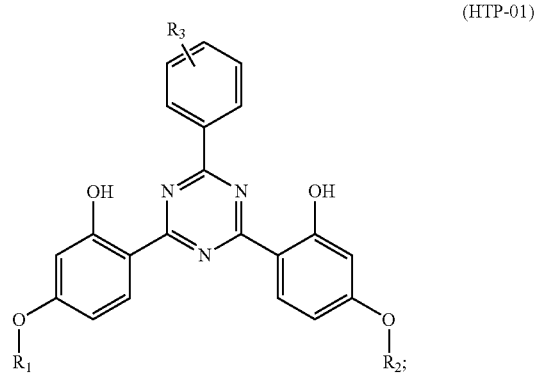

(HTP-01)

wherein
$R_1$ and $R_2$ independently from each other are $C_1$-$C_{18}$alkyl; and
$R_3$ is $C_1$-$C_{10}$alkoxy.

10. The composition according to claim 9, wherein the hydroxyphenyl triazine derivatives (B2) correspond to formula

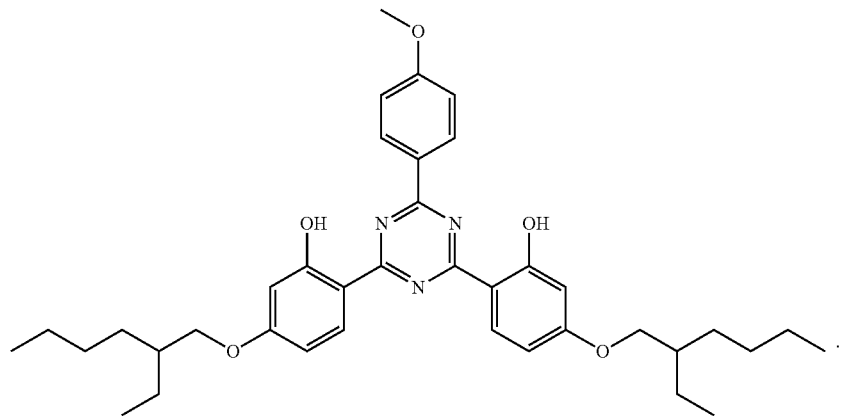

(HTP-02)

11. The composition according to claim 1, wherein the trianilino-s-triazine derivatives (B3) correspond to the formula

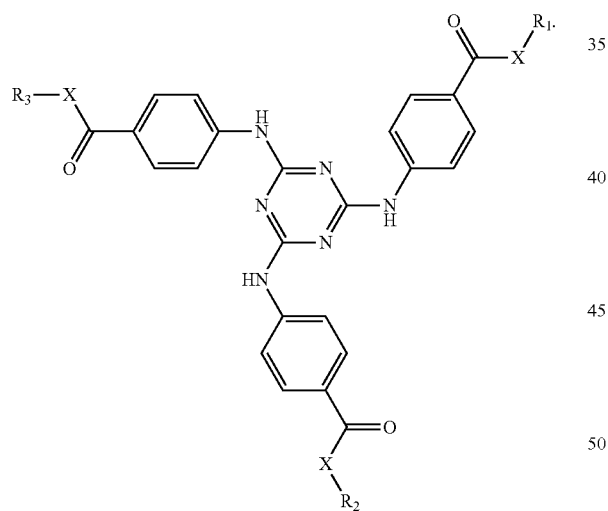

(TAT-01)

wherein $R_1$, $R_2$ and $R_3$ independently from each other are $C_1$-$C_{20}$alkyl, $C_6$-$C_{10}$aryl or $C_6$-$C_{10}$heteroaryl;

X is O; or $NR_4$; and $R_4$ is hydrogen; or $C_1$-$C_{20}$alkyl, aryl or heteroaryl.

12. The composition according to claim 11, wherein the trianilino-s-triazine derivatives (B3) correspond to the formula (TAT-02)

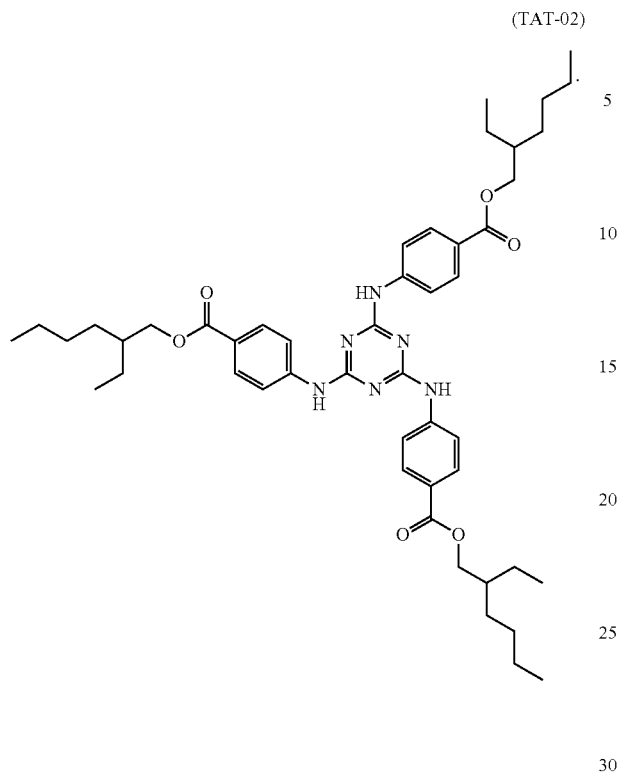

13. The skin care composition as claimed in claim 1, wherein the composition is in the form of a tablet soap, liquid soap, soapless detergent, washing paste, skin emulsion, or skin oil.

14. A cosmetic composition comprising (A) a solubilizing agent according to formula

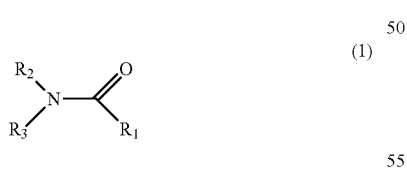

(1)

wherein $R_1$ represents $C_6$-$C_{24}$ alkyl;

$R_2$ and $R_3$ together with the linking nitrogen atom form a 5 or 6 membered heteroaromatic radical which optionally contains one or more nitrogen atoms and said heteroaromatic radical is optionally substituted by one or more $C_1$-$C_4$ alkyl, and (B) an organic UV filter according to the formula

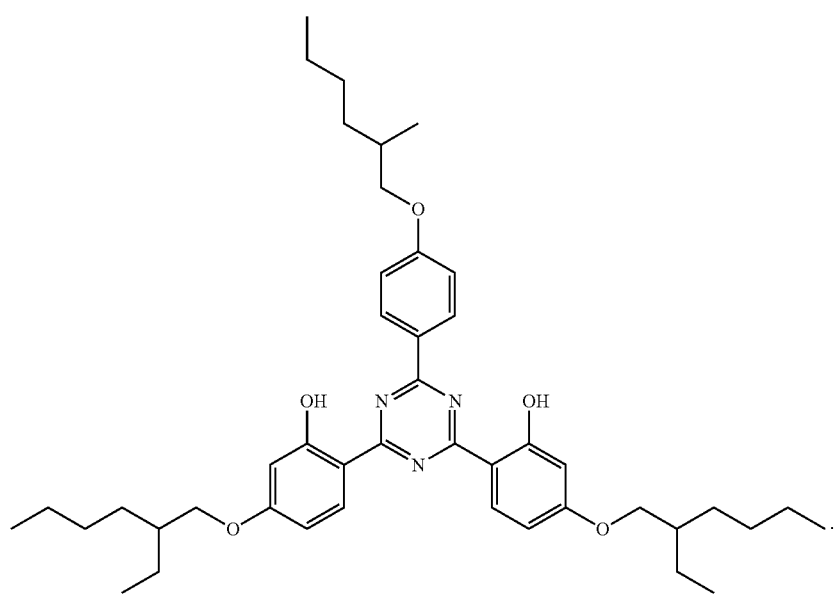
(HTP-03)
15. A cosmetic composition comprising
(A) a solubilizing agent according to formula 1, AM-01, or AM-02
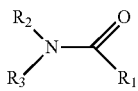 (1)
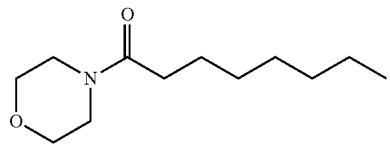 (AM-01)
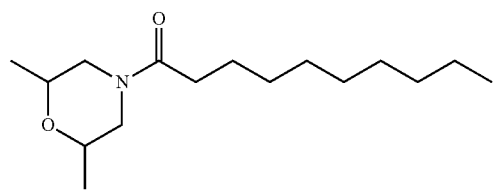 (AM-02)
wherein
$R_1$ represents $C_6$-$C_{24}$ alkyl;
$R_2$ and $R_3$ together with the linking nitrogen atom form a morpholine ring, which is optionally substituted by one or more $C_1$-$C_4$ alkyl, and
(B) an organic UV filter according to the formula

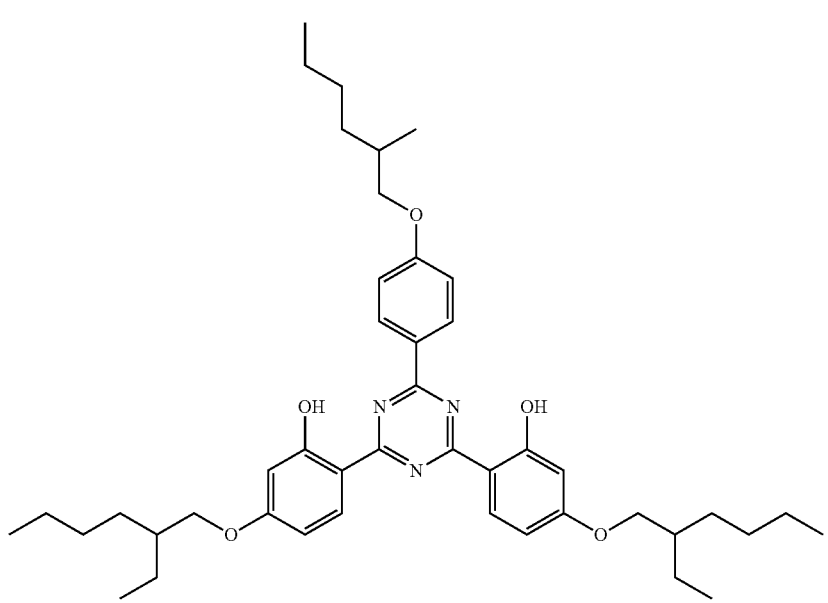

(HTP-03)

wherein the cosmetic composition optionally comprises an additional organic UV filter selected from the group consisting of (B1) benzophenone derivatives, (B2) hydroxyphenyl triazine derivatives; and (B3) trianilino-s-triazine derivatives.

16. The composition according to claim 15, wherein compound (A) corresponds to the compound of formula

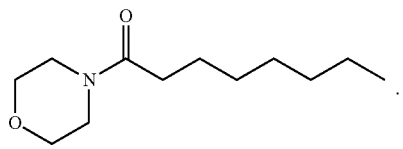

(AM-01)

17. The composition according to claim 15, wherein compound (A) corresponds to the compound of formula

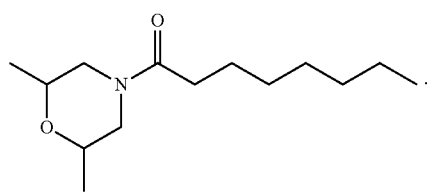

(AM-02)

18. A cosmetic composition comprising
(A) a solubilizing agent according to the formula

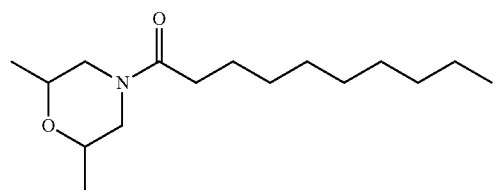

(AM-02)

and
(B) at least one organic UV filter selected from the group consisting of
(B1) benzophenone derivatives,
(B2) hydroxyphenyl triazine derivatives; and
(B3) trianilino-s-triazine derivatives.

* * * * *